United States Patent

Putz et al.

[11] Patent Number: 5,980,736
[45] Date of Patent: Nov. 9, 1999

[54] APPARATUS AND PROCESS FOR PROCESSING RAIN AND/OR SURFACE WATER

[76] Inventors: Leo Putz, Leo-Putz-Weg 1, D-82131 Gauting; Reinhard Witt, Alter Kirchweg 1, D-53562 St. Katharinen; Christian Putz, Leo-Putz-Weg 1, D-82131 Gauting, all of Germany

[21] Appl. No.: 08/897,578

[22] Filed: Jul. 21, 1997

[51] Int. Cl.⁶ .................................................. C02F 1/50
[52] U.S. Cl. ...................... 210/104; 210/108; 210/195.1; 210/199; 210/257.1; 210/258
[58] Field of Search ..................................... 210/104, 108, 210/195.1, 199, 252, 257.1, 258, 177, 739, 743, 752

[56] References Cited

U.S. PATENT DOCUMENTS

| | | |
|---|---|---|
| 1,678,766 | 7/1928 | Cawley . |
| 2,723,755 | 11/1955 | Robinson . |
| 2,988,221 | 6/1961 | Culp . |
| 3,441,956 | 4/1969 | Farnham . |
| 3,557,341 | 1/1971 | Keith, Jr. et al. . |
| 4,381,240 | 4/1983 | Russell . |
| 4,465,593 | 8/1984 | Wemhoff . |
| 4,659,459 | 4/1987 | O'Leary et al. . |
| 4,997,574 | 3/1991 | Sarunac . |
| 5,207,921 | 5/1993 | Vincent . |
| 5,422,014 | 6/1995 | Allen et al. . |
| 5,423,981 | 6/1995 | Krieger . |

*Primary Examiner*—Jay H. Woo
*Assistant Examiner*—Fred Prince
*Attorney, Agent, or Firm*—Oblon, Spivak, McClelland, Maier & Neustadt, P.C.

[57] ABSTRACT

The invention is directed to an apparatus for processing rain and/or surface water having a container for storing the water to be processed, a circulating arrangement for circulating the water to be processed in the container, a measuring arrangement for measuring the water quality of the water to be processed, and a processing arrangement for treating the water to be processed in dependence upon the water quality measured by the measuring arrangement.

20 Claims, 2 Drawing Sheets

APPARATUS AND PROCESS FOR PROCESSING RAIN AND/OR SURFACE WATER

BACKGROUND OF THE INVENTION

1. Field of the Invention

The invention relates to an apparatus and process for processing rain and/or surface water and particularly to an apparatus or a process for disinfecting and neutralizing atmospheric precipitation water.

2. Discussion of the Background

The importance of obtaining drinking water from atmospheric precipitation and surface water has increased in view of the increasing costs for obtaining and processing drinking water, the increasing problem for decontaminating rain water, and the increasing environmental protection awareness.

In commercially used apparatuses and processes, often extraordinary amounts of water must be used that do not necessarily have a number 1 drinking water quality. To counteract this, tests are being carried out in the private sector for substituting drinking water with rain and/or surface water. However, the results have been mediocre so far.

Conventionally, neither rain water nor surface water is physically filtered before running into containers (cisterns, rain water gathering containers, etc.). Additionally, this water is transferred to an intermediate container by means of a pump from which it is fed to the utilization appliances, for example, toilet tanks, dishwashers, washing machines, garden hoses, bulk consumers, etc. by means of so-called household waterworks. Other apparatuses are known which eliminate the intermediate container. If, during the summer, the water level in the gathering container or in the intermediate container is too low, a larger quantity of fresh water is fed into the gathering container or the intermediate container until the water level there is sufficient (typical value of rain water gathering receptacle: 300 to 500 1).

A disadvantage when introducing such quantities of fresh water into the gathering container or intermediate container is, however, that the fresh water or drinking water comes into contact with the container walls or the water comes from acid rain or contaminated water (industrial water). Due to this, the newly fed fresh water or drinking water is also contaminated and polluted. The utilization of such industrial water in the household systems known until now in the private sector requires, therefore, special appliances suitable for industrial water (for example, industrial water rinsing machines, industrial water washing machines, etc.). However, the prices are considerably higher in comparison to the apparatuses that use only drinking water. Such appliances that tolerate industrial water can, however, utilize industrial water for presoaking or cleaning, but they do need sterilized water for the last washing cycle. A second connection is necessary for providing drinking water from the drinking water supply.

Contaminated industrial water also cannot be utilized for toilet flushing without consequences. The glazing of the ceramic is more or less porous depending upon the firing. The microscopically small porous areas are attacked by the industrial water that is not pH-neutral and also by contaminants. This pollution can no longer be completely removed with strong chemicals. The consequences are a greenish coloring, slow destruction of the glazing, and therefore, depending on the quality of the glazing, a very short service life (one to two years).

SUMMARY OF THE INVENTION

The object of the invention is to provide an apparatus and process for processing rain and/or surface water that makes the utilization of conventional appliances in a cost-effective manner possible. It also protects the ceramic, pipelines, and distribution networks, as well as the structures that come into contact with the industrial water.

A commercial use, for example, for street washing, automobile plants, the recycling industry, or dry cleaning has often not been taken into consideration and not only because of the above-mentioned reasons.

The utilization of conventional household appliances is made possible in this way, at the same time protecting the ceramics, pipelines, and distribution networks, as well as the structures that come into contact with the processed water. Also, only reduced quantities of dispensed substances are used and only so much drinking water is fed into the appliance as is absolutely necessary, whereby an extremely cost-effective water processing installation is obtained.

The quality of the water can be brought to a preset desired value, particularly by using a measuring arrangement for measuring the water quality of the processed water and a processing apparatus that processes the water in dependence upon the measured quality of the water. A circulating arrangement further ensures an even circulation of the processed water, whereby a very uniform water quality is obtained.

The processing apparatus consists preferably of several storage containers where, for example, substances are stored that are used for increasing and decreasing the pH value, as well as substances for disinfecting the water. The substances are fed directly into the circulation by means of pumps and pipelines or pipes connected to each one of the storage containers, whereby a control arrangement determines the respectively fed substances in dependence upon the measured actual values and the desired values measured by the measuring arrangement. In this way, the water quality can be brought to the desired water quality in a short time by means of the control circuit consisting of the measuring arrangement, control electronics, and dispensing arrangement.

If the measuring arrangement is installed directly on the pipeline or pipe system of the circulating arrangement on a location on the side of the upflow of the feeding arrangement where the substances are fed, a measurement of the quality of the water can be carried out in a highly exact manner, while a defect of the circulation arrangement (for example, a pump defect) can be immediately recognized due to the sharp increase of the concentration value of substances in the measuring arrangement due to a lack in flow.

Two containers are obtained by using a partition wall, whereby untreated rain water for utilization in, for example gardens, is available in one container, while the water to be treated gathered in the other container is neutralized and sterilized and made available for the use in household appliances and other devices in the home. A third container can be obtained by using a second partition wall, which makes possible a concentrated treatment of the contaminated rain water fed by means of a suitable feeding of the circulation arrangement, which then feeds into a further, or basic, container for setting to the desired concentration or water quality.

In this way, each one of the containers has flow channels that further favor a uniform mixing of the water in each one of the containers. This thorough mixing can be increased by spinning the water that is fed back by means of the circulating arrangement at a suitable location.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Even though the apparatus for processing rain water and/or surface water can consist basically of only one container or more than two containers, two or three containers are used in the following preferred exemplary embodiments.

Exemplary Embodiment 1

Figure 1:
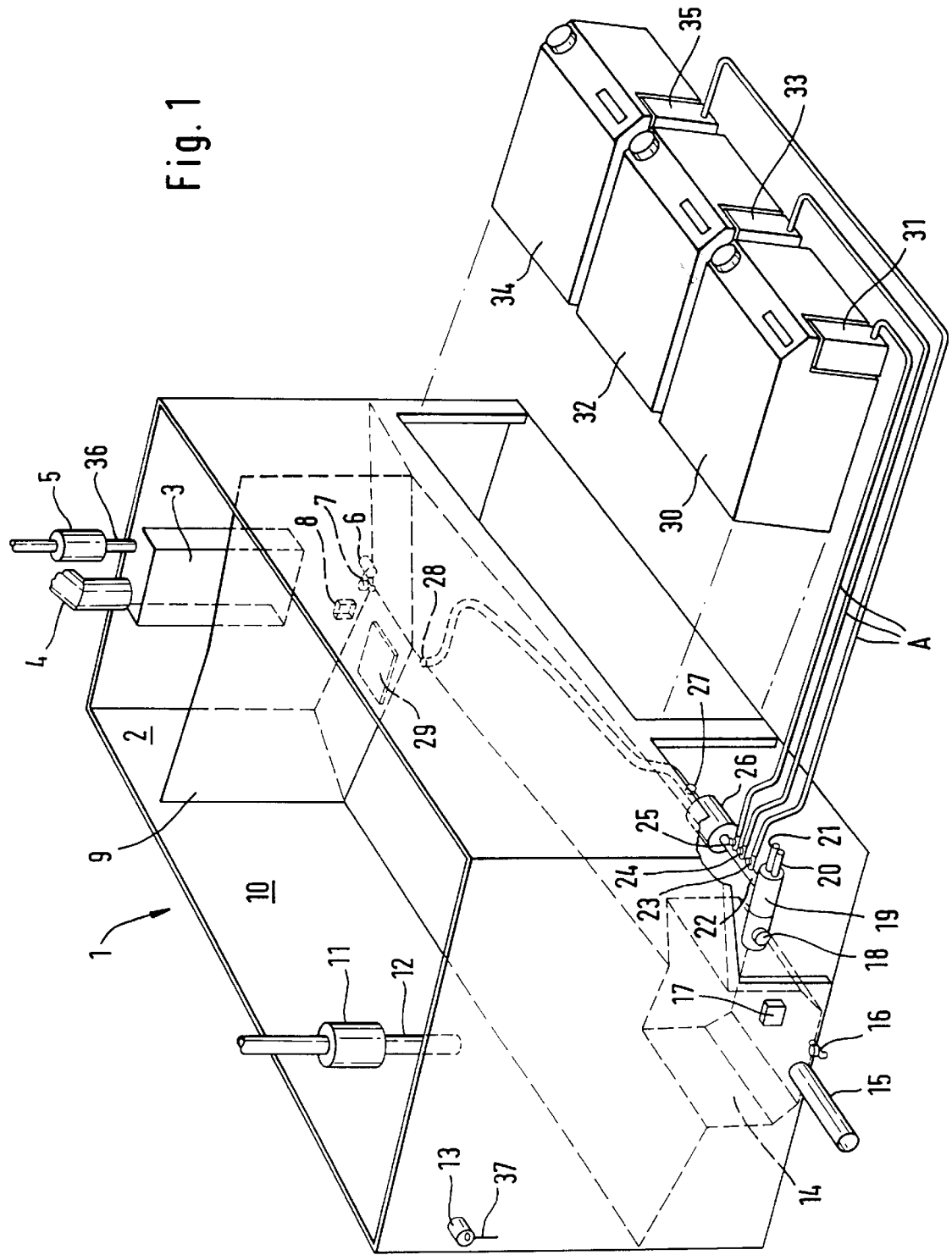
FIG. 1 is a perspective view of the apparatus for water processing according to a first exemplary embodiment of the invention.

FIG. 1 shows a perspective view of the apparatus for processing rain and/or surface water based on a first exemplary embodiment according to the invention.

In FIG. 1, the reference number 1 designates a basic container with a first container 10 for the water to be processed and a second container 2, wherein the untreated rain water flows from a gathering arrangement. The water inlet of this gathering apparatus is regulated by means of a control in dependence upon the determined filling level values. The filling of the basic container 1 is carried out by means of at least one rain water or industrial water inlet 4 that flows into a second container 2 by means of a channel 3 vertically installed that is open at the bottom. The channel or the flow channel 3 serves as water circulating or spinning means in the second container 2 during filling. The rain or industrial water in the second container 2 is not treated since it is intended, for example, for garden watering. The water supply of this gathering arrangement is regulated by means of a control according to the determined fill level values.

The water to be processed, or the industrial water, is found in the first container 10. For simplifying the construction and avoiding further supply lines—as will be described further—the first container 10 and the second container 2 are separated from each other by means of a partition wall 9. The filling of the first container 10 is carried out by means of the overflow of contaminated rain or industrial water from the second container 2 over the wall 9. A single flow direction must be set so that the water to be processed contained in the container 10 is not mixed with the contaminated water contained in the second container 2. This is achieved by keeping the water level in the first receptacle 10 lower than the level in the second bowl 2 in each case, which is ensured by means of an electronic control (not shown) or, if this control fails, by means of an overflow 13 of large dimensions.

When filling the first container 10, the deepest or lowest section 14 of the container 10 is naturally filled first. The determination of the water level in the first and second containers 10 and 2 is carried out by means of pressure sensors 17 and 8 flanged on the side. At the lowest point of the lowest section 14 of the first container 10 is a supply outlet 15 to which the consumers such as, for example, the household waterworks or each one of the household appliances or large consumers are connected directly. The containers 2 and 10 are preferably built V-shaped in the mid section and run off into their discharges 15 and 6 and their outlet faucets 16 or 7, whereby a complete discharge of the total of the liquid contained in container 1 is achieved. A circulation or a circulating arrangement is provided for a thorough mixing of the industrial water contained in the first container 10 or in the lowest section 14 for sending the water from a lowest point in the first container 10 to a highest point by means of the circulating arrangement which consists basically of faucets 18 and 27, a pipe 22, a pump 26, and a backflow 28.

A measuring arrangement for measuring the quality of the water to be processed consists of a measuring pipe 19 and measuring electrodes 20, 21, and 46. A redox value electrode 20, a pH value electrode 21, and a chlorine value electrode 46 are particularly used as measuring electrodes. FIG. 1 shows the measuring arrangement for measuring the quality of the water to be processed directly at the circulation or circulating arrangement. It can, however, be provided also on any other point within the first container 10 for the water to be processed, as long as it is always in contact with the water. The measuring values needed for the control, among others, are determined by this measuring arrangement.

In the exemplary embodiment shown in FIG. 1, the water to be processed flows from the lowest section 14 of the first container 10 through the faucet 18 into the measuring pipe 19, wherein one or several electrodes 20, 21, and 46 are installed, which measure the quality of the water to be processed. These electrodes are preferably sealed, but easily removable by means of PG screws. A pump 26 sends the water that flows slowly at first through the high section of the measuring pipe 19 from the lowest section 14 through the narrowed section in the pipe 22, where it flows faster, into the higher-lying mid level section of the first container 10. A splash protector 29 serves as distributor at high water level, or protects from leakage of treated water from the second receptacle 2 at low level.

A processing arrangement for treating the water to be processed consists basically of storage containers 30, 32, and 34 which, for example, can be installed under the first container 10, and each of the liquids or substances for disinfection as well as for increasing or decreasing the pH value. Pumps 31, 33, and 35 are provided for feeding each one of the substances contained in the storage containers 30, 32, and 34 that feed the liquids or substances into the industrial water circulation by means of feeding pipes or pipelines A. The pumps 31, 33, and 35 are built so that a backflow of the water of the circulation is not possible during standstill. The ends of the feeding pipes A can end in a narrowed section. The dispensing faucets 23–25 serve for separating the dispensing pipe from the circulation for, for example, carrying out maintenance work on the pumps 31, 33, 35 or the storage containers 30, 32, 34. The dispensation of each one of the substances is carried out in dependence upon the water quality values provided by the measuring arrangement, that is, the actual values of the water to be processed is undertaken by a control (not shown), for example, by means of the strokes of a pump 31, 33, 35.

The addition of dispensed substances is carried out preferably in the pipe 22 within the circulation. However, it can be fed into any other location in the water circulation of the first container 10. The water flow generated by the pump 26 takes with it then the introduced dispensed substance and distributes the same by means of the backflow 28 in the first container 10. This assembly possesses an advantage in that no dispensed substances reach the electrodes before flowing through the first container 10 with the pump 26 running. When there is a defect in the pump 26, however, due to the lack of flow, dispensed fluids or substances do reach the electrodes 20, 21, and 46 directly, whereupon an immediate switching off of the dispensing addition in the pipe 22 can take place. For avoiding a destruction or damage of the pump 26 due to chemical, often strongly reacting, dispensed substances, the pump 26 can also be installed on the upflow side of the circulation, whereby the chemical stress on the pump 26 can be reduced. The faucets 18 and 27 make possible a fast and relatively leak-free exchange of the electrodes 20, 21, and 46, as well as of the pump 26.

If it is impossible to provide a supply of industrial water when needed to the basic container 1 (for example, during droughts in the summer), then the supply of drinking water by means of the inlet pipes 12 and 36 is controlled by means of the electrically operated valves 5 and 11. Since, according to DIN 1988, drinking water cannot be mixed in closed pipeline systems with industrial water, an open transfer point between drinking water and industrial water must be provided. It is possible to use a small-volume external open container. An additional electrically controlled valve with corresponding pipe system, two valves in all, should be installed at the outlet of the open container as well as also at the outlet 15. The fill level measurement and an overflow into the external container should also be provided.

With the invention, such a cost-intensive installation and the installation of additional valves, their electronics, the container, and the pipelines can be eliminated as will be explained in the following description.

When there is a low fluid level in the first container 10 or in its lowest section 14, drinking water is fed by means of the electrically operated valve 11 and the inlet pipe 12 connected thereto. The inlet pipe 12 is installed in such a manner that its end lies considerably higher than the overflow 13 and ends directly over the small volume lowest section 14 of the first container 10. The lowest section 14 is also structured in the same size so that the pump of the household waterworks cannot suction in any air until the drinking water has fully flowed in, so that a minimum filling level is guaranteed at any time. The refilling of the lowest section 14 is carried out merely up to just below a preset limit in the first container 10 which is shown in FIG. 1 as the surface area of the first container 10. The pressure sensor 17 takes over the measurement of the liquid level, whereby the pressure sensor also measures the fill level of the lowest section 14 as well as the upper section of the container 10. A further advantage of this fill level regulation lies in that the electrodes 20, 21, and 46 in the measuring pipe 19 are held constantly humid since the electrodes generally should not be exposed to the air for longer periods of time to avoid strong drift occurrences of the measuring signals that would then falsify the measurements.

If only disinfected water or only drinking water is contained in the lowest section 14 of the first container 10, the circulation can be switched off since the water contained in the lowest section 14 does not require processing or treatment. It becomes contaminated only after it has been standing for several days (such as, for example, during vacation time). It is possible to activate the circulation automatically for a short period of time under conditions of "zero consumption of industrial water" and to undertake a water treatment in the lowest section 14 of the first container after a certain time or completely eliminate the same.

In the same way, a low liquid level in the second container 2 containing the garden watering water is completed with drinking water by means of the electrically operated valve 5 and its inlet 36. The drinking water inlet 36 ends also, just like the rain water or industrial water inlet 4, in the flow channel 3.

The complete filling of the second container 2 with drinking water is carried out similar to the first container 10. Only so much drinking water is fed by means of the drinking water inlet 36 as is necessary to avoid an air suction by a pump of the household waterworks until the filling with drinking water is completed. An eventual failure of the electronics would not be critical in this case, since the industrial water supply for the first container 10 is carried out by means of the overflow of the second container 2. The normal disinfection process described above is used if there is an availability of rain and/or surface water in the gathering arrangement or if there are sudden changes of the fill level of container 1. The overflow 13 is only flooded with water if there are function disturbances or a failure of the control electronics. A sensor 37 built into the outlet can, in this way, recognize the disturbance, trigger an alarm, and effect and emergency shut-off of the system.

Exemplary Embodiment 2

Figure 2:
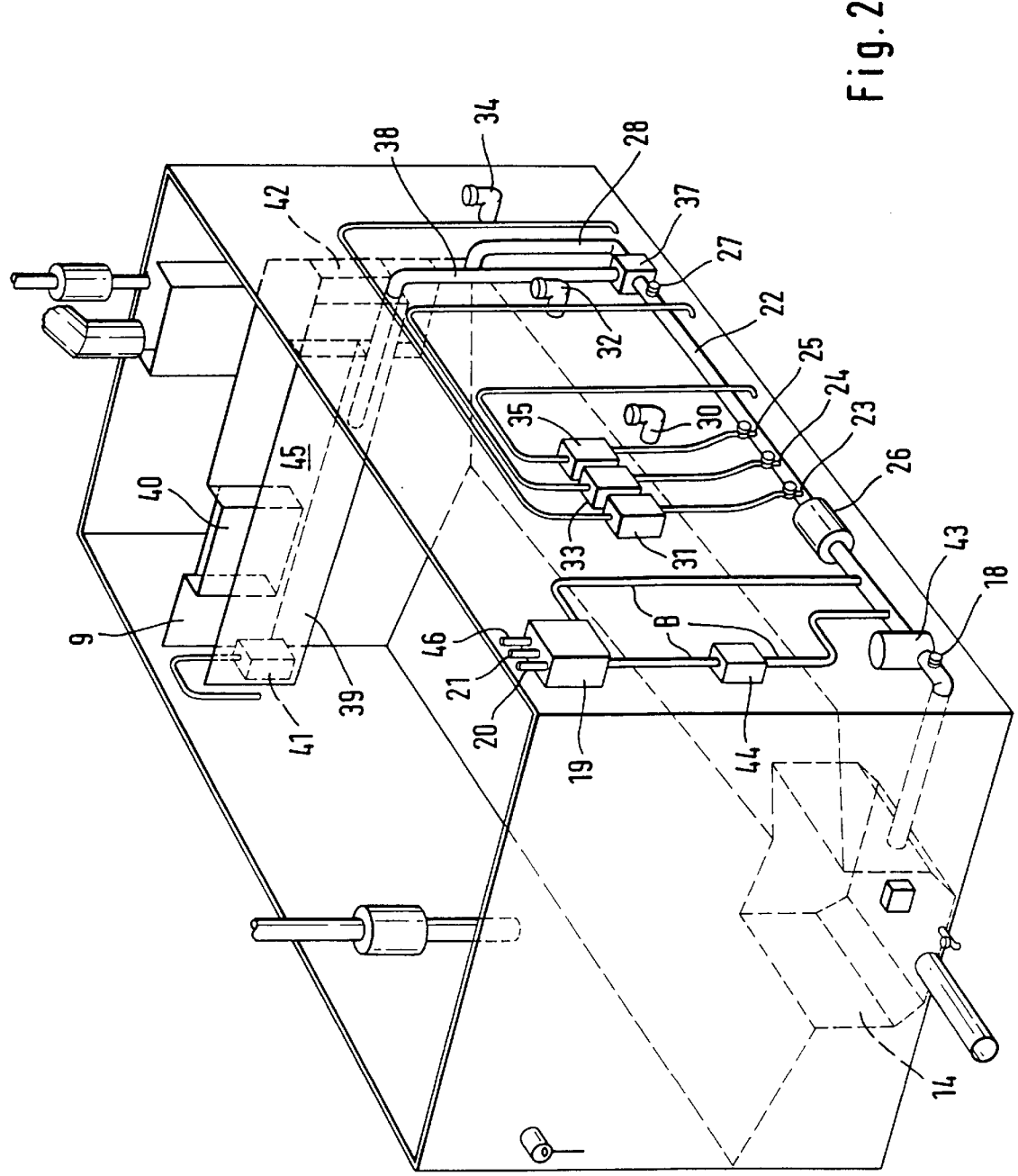
FIG. 2 is a perspective view of the apparatus for water processing according to a second exemplary embodiment.

FIG. 2 shows a perspective view of the apparatus for processing rain and/or surface water according to a second exemplary embodiment.

The same reference numerals have been used for the same respective components as in the apparatus of FIG. 1 and therefore no further description of the same is provided.

The apparatus for water processing according to the second exemplary embodiment of the invention differs from the apparatus of FIG. 1 mainly in that a third container or intermediate container 39 is provided. The filling of the first container 10 is carried out in a series of steps: the contaminated water flows by overflow of the second container 2 over the partition wall 9 through the flow channel 40 into the intermediate container or third container 39. From this third container 39, the water flows again by overflow through a further flow channel 42 into the first container 10. The flow channels 40 and 42 carry out the same function of the flow channel 3 and effect a thorough mixing of the water in each one of the containers. The task of the third container 39 is to provide a secure separation of the water of the second container 2 from the water of the first container 10. Due to this arrangement, no untreated residual water from the second container 2 can enter into the first container 10. This is particularly necessary during a continuing treatment of the water after disinfection in the first container 10.

Contrary to the first exemplary embodiment of the invention, the second exemplary embodiment possesses a modified circulation. The reference numeral 37 refers to a distribution apparatus for separating the backflow water from the water provided with dispensed substances by means of the backflow 28 into the first container 10 and a further backflow 38 into the third container 39. During disinfection, the water from the lowest section 14 of the first container 10 can flow by means of the circulation either through the distribution apparatus 37 and the backflow 28 in the upper section of the first container 10, and/or through the distribution apparatus 37 and the backflow 38 into the third container 39. The advantage lies in the possibility of adding targeted and concentrated dispensed substances to the water coming from the second container 2 and flowing into the third container 39 so as to shorten the total treatment time.

As an alternative to the exemplary embodiments shown in FIG. 2, other exemplary embodiments are possible wherein only one substance is fed into the water to be processed from the third container 39 or a further intermediate container whereby, for example, a neutralization can be separated from the disinfection of the water to be processed and wherein, for example, untreated contaminated rain water or disinfected water, as well as disinfected water and pH-neutralized water can be prepared separately and gathered in the different containers. In this case, separately operated circulating arrangements or circulations are used, wherein only one dispensed substance is fed for treating the water.

As described above, during non-availability of industrial water (for example, drought in the summer), only the lowest section 14 of the first container 10 is filled. In this case, the third container 39 should run dry. If this is technically impossible by means of the distribution apparatus 37 (for example, in pressurized systems), then it is possible to carry out this function by means of an apparatus 41 (for example, a pump, a decompressed opening of a magnetic valve, etc.) which feeds the water of the third container 39 into the first container 10.

The flow channels 40 and 42 have the task to guide the water that runs through them to the containers 39 and 10. A rapid and particularly effective thorough mixing or spinning of the industrial water is achieved in connection with the backflow 38 or 28, either on the side or directly opposite the opening of the flow channel 40 or 42.

The measuring arrangement 19, 20, 21, and 46 can be inserted directly into the circulation depending on the system's inherent technical guidelines. In most cases, however, for an exact determination of the measuring values, an even water flow must be provided through the measuring arrangement 19. This requirement is satisfied by means of a pump 44 which maintains the throughflow constant eventually by means of a sensor that is connected to the pump or integrated into the same. The measuring circulation represented in FIG. 2, consisting of the pump 44, the measuring pipe 19, and the measuring electrodes 20, 21, and 46, can be repeated to ensure redundance and the highest possible accuracy of the measuring values.

The storage containers 30, 32, and 34 for the dispensed substances for treating the water to be processed can be attached to the system or be mobile such as, for example, as inserts or externally. The attached variation is represented in the second exemplary embodiment of FIG. 2. Finally, the circulation described above can be completed by a prefilter 43 with integrated backflow rinsing arrangement. In this way, penetrating contamination such as, for example, dead algae, can be filtered out of the water before it flows into the container 1 and particularly before it flows into the measuring pipe 19. A cleaning of the filter 43 is achieved by means of the backflow rinsing arrangement.

In the apparatus for processing rain and/or surface water according to the second exemplary embodiment of the invention, untreated rain or surface water is stored in the second container 2, for example, for garden use. The third container 39 is particularly useful when an electrolysis arrangement or an apparatus for removing disinfection substances is used. In this way, the contaminated water from the container 2 cannot drip directly into the first container 10, since uncontaminated water without additives is stored after treatment in the third container 39. A constant circulation takes place from the first container 10 to the third container 39 by means of the circulating arrangement and the distribution apparatus 37, and the distribution apparatus 37 consists preferably of a two-way valve or two magnetic valves. The circulation takes place only within the container 10 during the disinfection substance removal. The disinfection and disinfection substance removal takes place in the first container 10.

The inserted measuring circulation, consisting of the booster pump 44, the measuring pipe 19, and the measuring electrodes 20, 21, and 46, makes easier, among other things, the exchange or eventual calibration of the electrodes and serves for maintaining a constant flow.

What is claimed as new and is desired to be secured by Letters Patent of the United States is:

1. Apparatus for processing rain or surface water comprising:

a container for containing the water to be processed;

a circulating arrangement for circulating the water to be processed in the container wherein the circulating arrangement includes a pump, a pipe system, and a back flow, where the water to be processed is guided from a lowest section of the container to an upper section;

a measuring arrangement for measuring actual values which show the quality of the water to be processed; and a processing arrangement for treating the water to be processed in dependence upon the actual values measured by the measuring arrangement and preset desired values for the quality of the water to be processed wherein said processing arrangement includes a storage arrangement for storing substances for treating the water to be processed, a feeding arrangement for feeding the substances of the storage arrangement into the water to be processed and a control arrangement which controls the feeding arrangement in dependance upon the actual values measured by the measuring arrangement and thereby dispenses the substances.

2. Apparatus according to claim 1, characterized in that the feeding arrangement feeds the substances directly into the water to be processed contained in the pipe system of the circulating arrangement.

3. Apparatus according to claim 2, characterized in that the feeding arrangement is arranged into the pipe system of the circulating arrangement on an upflow side of the pump.

4. Apparatus according to claim 2, characterized in that the measuring arrangement is arranged directly in the pipe system of the circulating arrangement.

5. Apparatus according to claim 4, characterized in that the measuring arrangement is arranged on an upflow side of the feeding arrangement.

6. Apparatus according to claim 2, characterized in that the measuring arrangement is connected to the pipe system of the circulating arrangement by means of a measuring pipe system and an additional pump.

7. Apparatus according to claim 1, characterized in that a first partition arrangement is provided, which partitions the container into a first container, where the treatment of the water to be processed takes place by means of a processing arrangement, and a second container where no treatment of the water takes place.

8. Apparatus according to claim 7, characterized in that at least a second partition arrangement is provided which, together with the first partition arrangement forms at least a third container, where a concentrated treatment of the water takes place by means of a processing arrangement and wherein said second partition provides effective separation of the water in the first container from the water in the second container.

9. Apparatus according to claim 7, characterized in that each one of the containers have a flow channel at the inlet for a thorough mixing of the water in each container.

10. Apparatus according to claim 7, characterized in that the partition arrangement is structured as an overflow partition wall, whereby filling of the separate containers is carried out partially by means of overflowing the containers.

11. Apparatus according to claim 8, characterized in that the circulating arrangement has a distribution arrangement that moves the water to be processed equilaterally or by means of backflows in the first container and in said at least third container.

12. Apparatus according to claim 1, characterized in that the backflow of the circulating arrangement is arranged on the side of or opposite to an inlet of each one of the containers, whereby a thorough mixing of the water is improved.

13. Apparatus according to claim 1, characterized in that a splash protection is provided near the backflow, whereby a backflow of the treated water into a second container containing the untreated water is impeded.

14. Apparatus according to claim 7, characterized in that the first and second containers each have at least one sensor for measuring a fill level.

15. Apparatus according to claim 7, characterized in that the containers each have a drinking water inlet which complements the container with the drinking water when a fill level falls below a preset value.

16. Apparatus according to claim 1, characterized in that the container has an overflow with a sensor which triggers an alarm and avoids a further feeding of water into the container.

17. Apparatus according to claim 4, characterized in that the circulating arrangement has a filter that removes impurities from the water to be processed.

18. Apparatus according to claim 17, characterized in that the filter is a filter with backflow rinsing arrangement and is arranged before the measuring arrangement.

19. Apparatus according to claim 1, characterized in that at least one additional measuring arrangement is provided, whereby a redundance and a disturbance-free measurement of the actual values that indicate the quality of the water to be processed is ensured.

20. Apparatus according to claim 8, characterized in that a discharge arrangement is provided in the third container, wherewith the third container can be emptied.

* * * * *

UNITED STATES PATENT AND TRADEMARK OFFICE
CERTIFICATE OF CORRECTION

PATENT NO. : 5,980,736
DATED : November 9, 1999
INVENTOR(S) : Leo PUTZ et al.

It is certified that error appears in the above-identified patent and that said Letters Patent is hereby corrected as shown below:

On the title page, item [30], the Foreign Application Priority Data is missing. It should be:

--[30] Foreign Application Priority Data

Jul. 20, 1996  [DE]  Germany...................19629305.7--

Signed and Sealed this

Twenty-eighth Day of November, 2000

Attest:

Q. TODD DICKINSON

*Attesting Officer*     *Director of Patents and Trademarks*